US008200004B2

(12) United States Patent
Michelsson et al.

(10) Patent No.: US 8,200,004 B2
(45) Date of Patent: Jun. 12, 2012

(54) METHOD FOR INSPECTING A SURFACE OF A WAFER WITH REGIONS OF DIFFERENT DETECTION SENSITIVITY

(75) Inventors: Detlef Michelsson, Wetzlar-Naunheim (DE); Joerg Richter, Weilburg (DE)

(73) Assignee: Vistec Semiconductor Systems GmbH, Weilburg (DE)

( * ) Notice: Subject to any disclaimer, the term of this patent is extended or adjusted under 35 U.S.C. 154(b) by 612 days.

(21) Appl. No.: 12/316,117

(22) Filed: Dec. 9, 2008

(65) Prior Publication Data

US 2009/0161942 A1 Jun. 25, 2009

(30) Foreign Application Priority Data

Dec. 20, 2007 (DE) ........................ 10 2007 047 933

(51) Int. Cl.
*G06K 9/00* (2006.01)
*G01N 21/86* (2006.01)
*G01V 8/00* (2006.01)
*H04N 7/18* (2006.01)
*G06F 3/048* (2006.01)

(52) U.S. Cl. .................. 382/148; 250/559.05; 348/125; 715/764

(58) Field of Classification Search .................. 382/141, 382/145, 148, 173, 174; 250/559.01, 559.04, 250/559.05, 559.07, 559.08; 348/125, 126, 348/128; 715/700, 764
See application file for complete search history.

(56) References Cited

U.S. PATENT DOCUMENTS

| | | | | |
|---|---|---|---|---|
| 4,406,545 | A | 9/1983 | Montone et al. | 356/380 |
| 4,795,260 | A | 1/1989 | Schuur et al. | 356/400 |
| 5,764,536 | A * | 6/1998 | Yamamoto et al. | 701/81 |
| 7,016,031 | B2 * | 3/2006 | Chen et al. | 356/237.2 |
| 7,130,055 | B2 | 10/2006 | Borden et al. | 356/491 |
| 7,164,410 | B2 * | 1/2007 | Kupka | 345/156 |
| 7,206,443 | B1 * | 4/2007 | Duvdevani et al. | 382/149 |
| 7,583,832 | B2 * | 9/2009 | Okuda et al. | 382/141 |
| 2005/0031189 | A1 | 2/2005 | Richter | 382/145 |
| 2005/0117017 | A1 | 6/2005 | Baer | 348/87 |
| 2007/0156379 | A1 * | 7/2007 | Kulkarni et al. | 703/14 |
| 2008/0250384 | A1 * | 10/2008 | Duffy et al. | 716/21 |

FOREIGN PATENT DOCUMENTS

| | | |
|---|---|---|
| DE | 103 31 594 | 1/2005 |
| KR | 100652297 | 11/2006 |

* cited by examiner

*Primary Examiner* — Michael A Lyons
(74) *Attorney, Agent, or Firm* — Davidson, Davidson & Kappel, LLC

(57) ABSTRACT

The invention relates to a method for inspecting a surface of a wafer with regions of different detection sensitivity. For this purpose, an image of the selected surface of the wafer is acquired using a detector. At least one region handled with a different detection sensitivity than the rest of the wafer may be defined on the surface of the wafer by means of an input unit. The detection sensitivity set for the regions is a percentage less than the detection sensitivity for the surface of the wafer without the regions with the different detection sensitivity.

19 Claims, 9 Drawing Sheets

1 3 8 2a 2b 7 6

METHOD FOR INSPECTING A SURFACE OF A WAFER WITH REGIONS OF DIFFERENT DETECTION SENSITIVITY

This claims priority of German Patent Application No. 10 2007 047 933.8, filed on Dec. 20, 2007 and hereby incorporated by reference herein.

The present invention relates to a method for inspecting a surface of a wafer with regions of different detection sensitivity. In particular, the present invention is used for macro-detection or macro-inspection.

BACKGROUND

German published patent application DE 103 31 594 discloses a method for inspecting structures on semiconductor substrates. After an image of the semiconductor substrate has been acquired, the various structural elements are allocated to various regions. Generally, these regions are referred to as regions of interest (ROI). These ROIs may automatically be transferred to corresponding structural elements of the semiconductor substrate. Different inspections or inspections with different inspection parameters are conducted in the various ROIs corresponding to the structure of the semiconductor elements to be evaluated. This method relates to the micro-inspection of the semiconductors.

Korean Patent 100652297 B1 discloses a method for detecting nuisance defects in semiconductors. A defect on the wafer is detected by setting a manual threshold. Another defect on the wafer is discovered by modifying this threshold.

U.S. Pat. No. 4,795,260 discloses a device for locating and testing areas of interest on a wafer. It is often important and necessary to examine a wafer immediately after a processing step to find out whether this processing step has been carried out according to the specifications. One way to achieve this is the so-called 5-point test, in which five unpatterned regions on the wafer are approached.

U.S. Patent Application No. 2005/0117017 A1 discloses a system and a method for imaging regions of interest (ROI). A camera uses a map to find more than two regions within the field of view of a camera in an image. The map identifies selected pixels of the image located within the ROI. The image data corresponding to those of the image may be stored, and the image data corresponding to those in the ROI are processed. The camera may be integrated in an optical inspection system to analyze ROI segments on the surface of a target.

SUMMARY OF THE INVENTION

It is an object of the present invention to provide a method improving the detection of defects on the wafer surface. This method is intended to be employed in the detection of the front-side of a wafer, the backside of the wafer and also in the edge detection of the wafer.

The present invention provides a method for inspecting a surface of a wafer with regions of different detection sensitivity, comprising the steps of:

acquiring an image of the surface of the wafer with the help of a detector, configured as a line sensor or a area sensor;

displaying the image of the wafer on a display;

defining via the display by means of an input unit at least one region on the surface of the wafer that is subjected to a different detection sensitivity than the rest of the surface of the wafer, wherein the detection sensitivity specified for the regions on the surface is a percentage less than the detection sensitivity for the surface of the wafer without the regions with the different detection sensitivity; and specifying parameters or a way of acquiring the image of the surface of the wafer for the regions on the surface of the wafer to be handled with a different detection sensitivity, also by means of the input unit.

The method for inspecting a surface of a wafer with regions of different detection sensitivity includes first the step of acquiring an image of a selected surface of the wafer with the help of a detector. As mentioned above, the surface of the wafer may be the front-side of the wafer or the backside of the wafer. Generally, the front-side of the wafer carries the patterned semiconductors. The image of the wafer is shown on a display. Regions on the surface of the wafer that are handled with a different detection sensitivity than the rest of the wafer may be defined via the display with the help of an input unit. Generally, it is sufficient to define a single region on the surface of the wafer that is handled with a different detection sensitivity. The detection sensitivity specified for the selected regions is a percentage less than the detection sensitivity for the rest of the wafer surface that does not contain any regions of different detection sensitivity. The input unit may also be used to specify the parameters or the way of acquiring the image of the surface of the wafer for the regions that are handled with a different detection sensitivity.

The detector used for the image acquisition of the front-side or the backside of the wafer may be a CCD line or a CCD chip.

A user interface is displayed on the display, with the help of which a user sets the parameters necessary for the detection and provides settings for image acquisition and image evaluation.

Several windows may be displayed on the user interface. In a first window displayed on the user interface, the user may supply input regarding the macro-detection of the wafer. A button is provided, via which the inspection of the surface of the wafer with regions of different detection sensitivity is initialized.

In a second window displayed on the user interface, there may also be supplied input regarding the macro-detection of the front-side or the backside of the wafer. There is also provided a button, via which the inspection of the selected surface of the wafer with regions of different detection sensitivity is initialized.

In a third window also displayed on the user interface, input regarding the parameters with respect to the shape of the at least one region inspected with a different detection sensitivity may be set.

Several regions inspected with a different detection sensitivity are listed in the third window. An identification number is assigned to each of the regions, wherein a percentage for a sensitivity of the pixel detection of the detector, a sensitivity of the gradient detection and a sensitivity for a local color detection is assigned to each of the regions for the inspection of the front-side of the wafer.

Similarly, several regions inspected with a different detection sensitivity may be listed in the third window. Again, an identification number is assigned to each of these regions. A percentage for a sensitivity of the pixel detection of the detector in the bright field, a sensitivity of the pixel detection in the dark field and a sensitivity for a color detection in the bright field is assigned to each of the regions for the inspection of the backside of the wafer.

The at least one region detected with a different detection sensitivity is a polygon, a rectangle or an object edited by the user.

Several regions, each of which may be examined with a different detection sensitivity, may be defined in the image of the surface of the wafer. The shape of the regions and the detection parameters of the regions may be set as desired.

The regions defined on the surface of the wafer that may be examined with a different detection sensitivity may be modified or deleted by means of an input means.

In the case that the region on the surface of the wafer to be examined with a different detection sensitivity is a polygon, the polygon is created such that more than three corner points are created in the image of the surface of the wafer with the help of the input means. It is important that the corner points for the definition of the polygon are not located on a straight line.

If there is an overlap of the polygon with a region of the wafer not having a chip patterned thereon, the detection is only performed on the region of the polygon containing the chips patterned for the front-side of the wafer. It is also possible that, in the case of an overlap of the polygon with an edge region of the wafer not occupied by any chip, the detection is only performed in the region of the polygon not containing any patterned chips on the front-side of the wafer. The region of the polygon not containing any chips on the surface of the wafer is displayed to the user in another color or with another pattern than the region of the polygon including chips.

If there are several overlapping regions each of which is to be examined with a different detection sensitivity, wherein the regions differ with respect to the parameters for the detection sensitivity, the parameters valid for the region last input are used for the region of the overlap. Generally, the region last input is defined such that it is on the top of the stack of regions. The order of the overlapping regions may be changed by means of the input means, wherein the detection in the overlap region is always done with the parameters corresponding to the region located on the top.

BRIEF DESCRIPTION OF THE DRAWINGS

In the following, embodiments will explain the invention and its advantages in more detail with reference to the accompanying drawings, in which.

DETAILED DESCRIPTION

Figure 1:
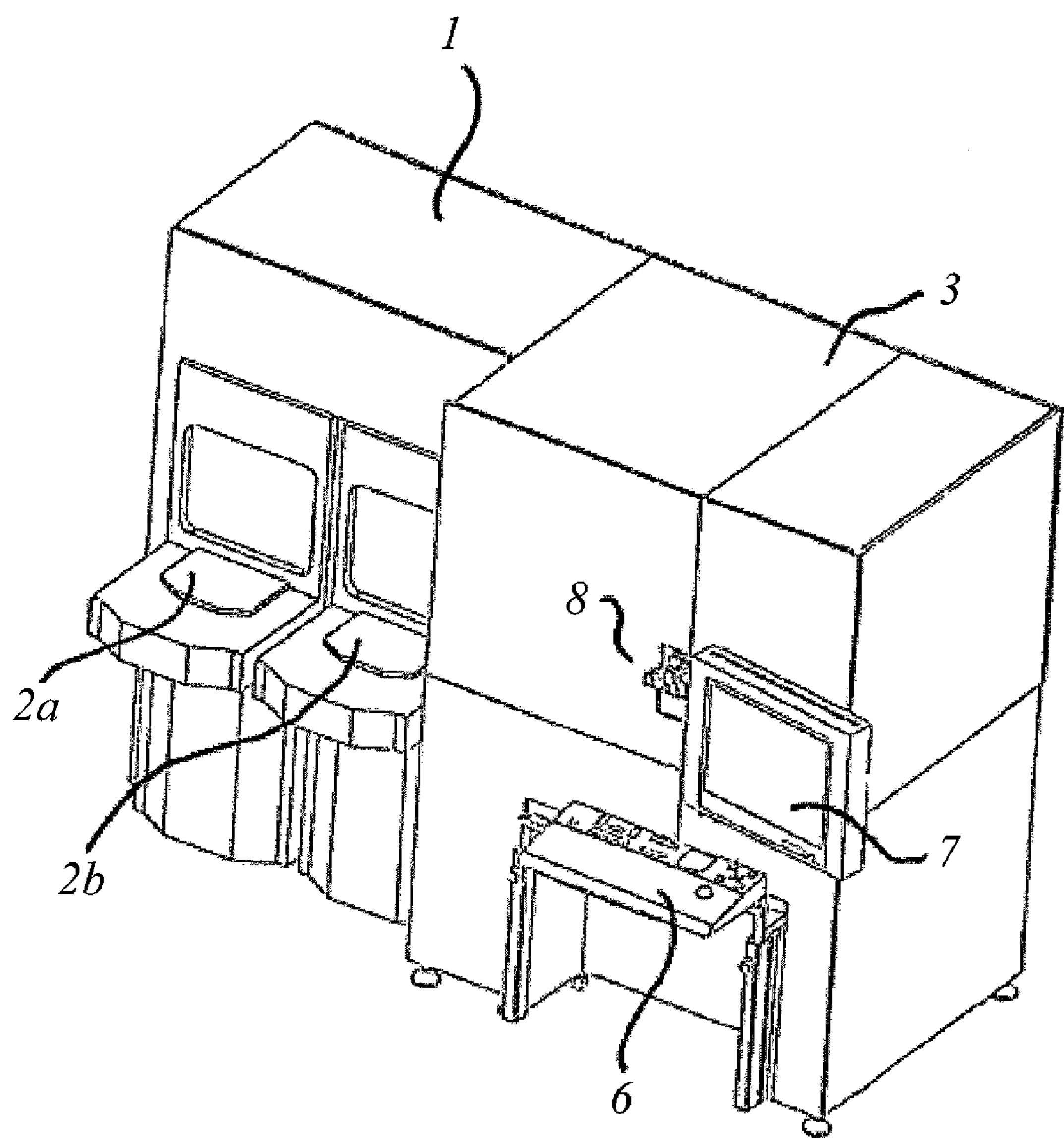
FIG. 1 shows a perspective view of a device allowing the inspection of the front-side and/or backside of a wafer.

FIG. 1 shows a perspective view of a device 1 with which images of the surface of a substrate may be acquired. Generally, the substrate is a wafer having a front-side carrying the patterned semiconductors. No structures are provided on the backside of the wafer. The device comprises two input ports 2*a* and 2*b*, via which the device is supplied with wafers. In a subunit 3 of the device 1, the images of the front-side and/or the backside of the wafer may, for example, be acquired. There may additionally be provided a microscope 8, via which a user may perform microscopic inspections of the surface of the wafer or of parts of the surface of the wafer. The image of the surface of the wafer acquired in the device 1 is displayed to a user on the display 7. In addition to the image of the surface of the wafer, the display 7 also shows several user interfaces, via which the user may supply input regarding the inspection of the wafer. There is further an input unit 6 for the user, via which the user may perform parameter modifications for the examination and/or inspection of the surface of the wafer. The input unit may be a keyboard, a mouse, a track ball and/or a joystick.

Figure 2:
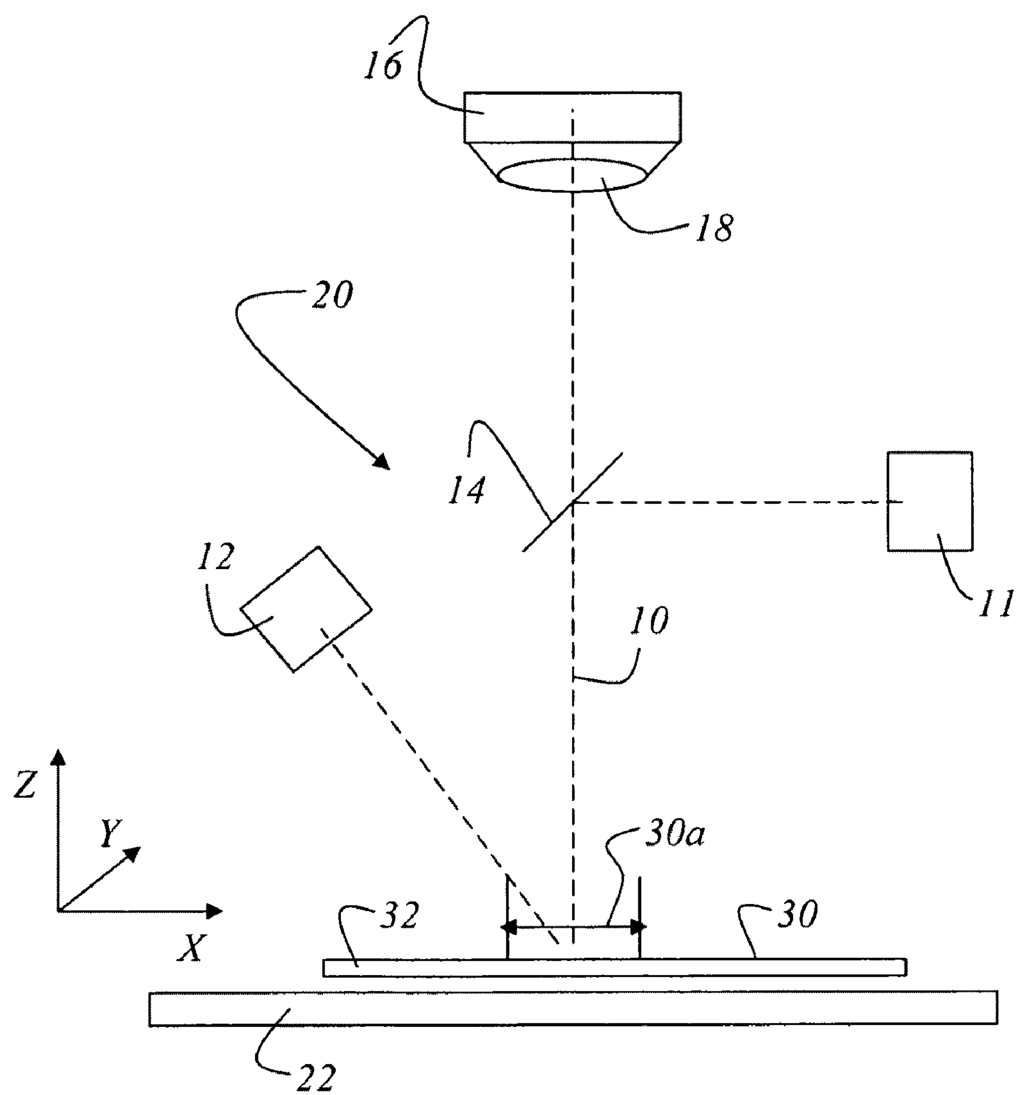
FIG. 2 shows a schematic optical setup that may be used for acquiring an image of the front-side and/or the backside of a wafer.

FIG. 2 shows a schematic representation of the optical means or optics 20 for acquiring an image of the front-side 30 or the backside 31 of a wafer 32. The wafer 32 is deposited on a table 22 movable in the X-coordinate direction and in the Y-coordinate direction. At least one incident light illumination means or illuminator 11 and at least one dark field illumination means or illuminator 12 are provided for the illumination of the surface of the wafer. The detector 16 allows converting the light coming from the surface 30 of the wafer 32 into electrical signals. At least one optical element 18 is provided to image the light on the detector 16. In the embodiment shown, the light of the incident light illumination means 11 is launched into the optical detection path 10 of the detector 16 via a beam splitter. In the embodiment shown, the entire surface of the wafer is captured by means of a so-called meander scan. This means that one band 30*a* of the part of the surface 30 of the wafer is captured at a time. It is also contemplated to capture the entire surface of the wafer in one go. Although the description of FIG. 2 only considers capturing the surface of the wafer by means of a meander scan, this is not to be considered as limiting the invention. Someone skilled in the art knows many ways how to acquire a macroscopic image of the surface (front-side and/or backside) of a wafer.

Figure 3:
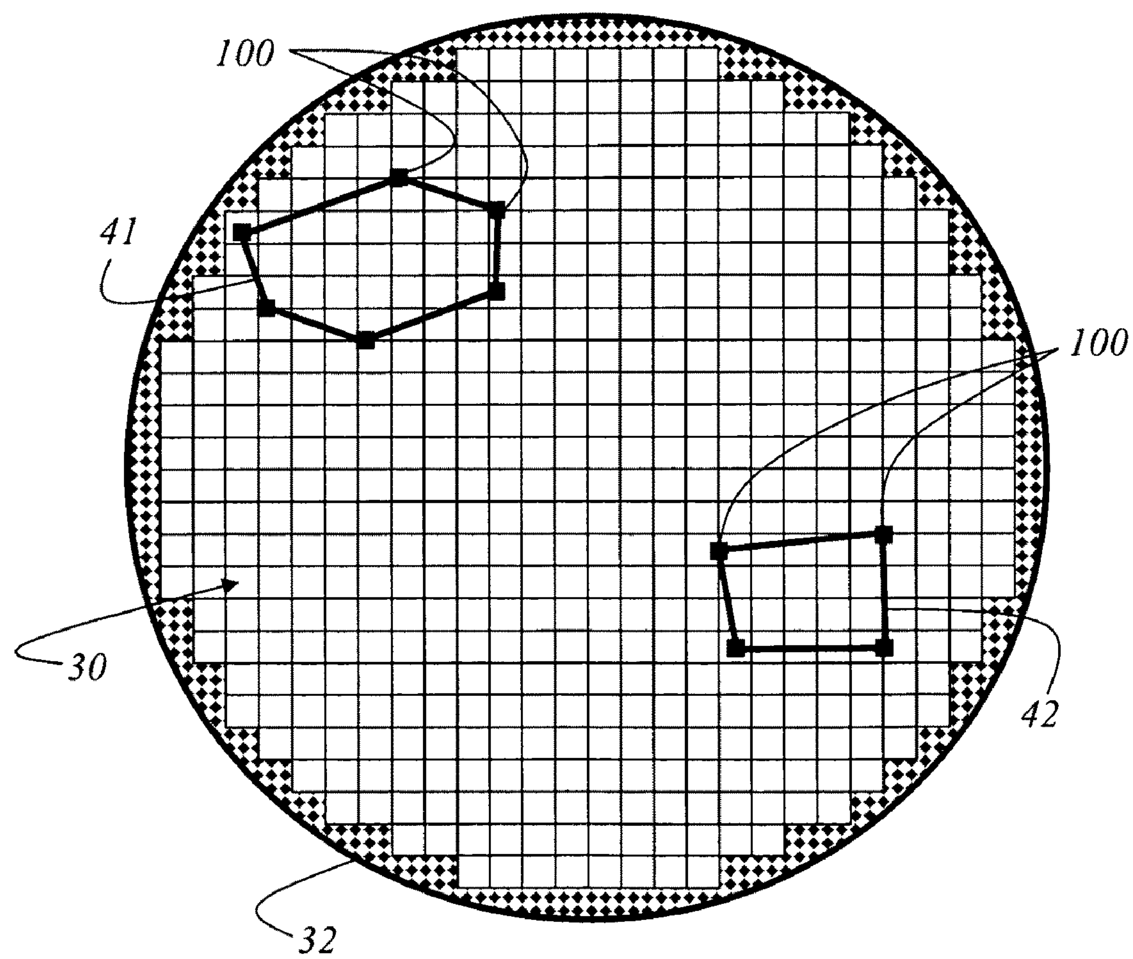
FIG. 3 shows a schematic view of an acquired image of the front-side of a wafer where several regions are defined that are handled with a different detection sensitivity.

FIG. 3 shows a top view of the front-side 30 of a wafer 32. As mentioned above, the front-side 30 of the wafer carries the patterned semiconductor structures. A first polygon 41 and a second polygon 42 are defined on the front-side 30 of the wafer 32. These two polygons 41 and 42 specify the regions that are handled with a different detection sensitivity than the rest of the wafer 32. Each of the polygons 41 and 42 is defined by a corresponding number of corners 100. The polygons may be defined by the user. For this purpose, the image of the front-side 30 of the wafer is displayed on the display 7 of the device 1. With the help of an input unit, the user may specify several corner points 100 around the region on the front-side 30 of the wafer, which are then connected to form the corresponding polygon. A different detection sensitivity than on the rest of the wafer is then used within this region.

In one possible embodiment, the polygons 41 or 42 may be drawn as follows. The computer mouse is used as input means. The left mouse button is used to set the corners 100. Then the mouse pointer holds a new corner 100 and draws a line from the previous corner 100. This means that the displayed polygon is always closed if the number of corners 100 is larger than 2. The polygon is finished with the right mouse button. Then the last variable corner is deleted. If the number of corners 100 is less than 3, the whole polygon is deleted.

Figure 4:
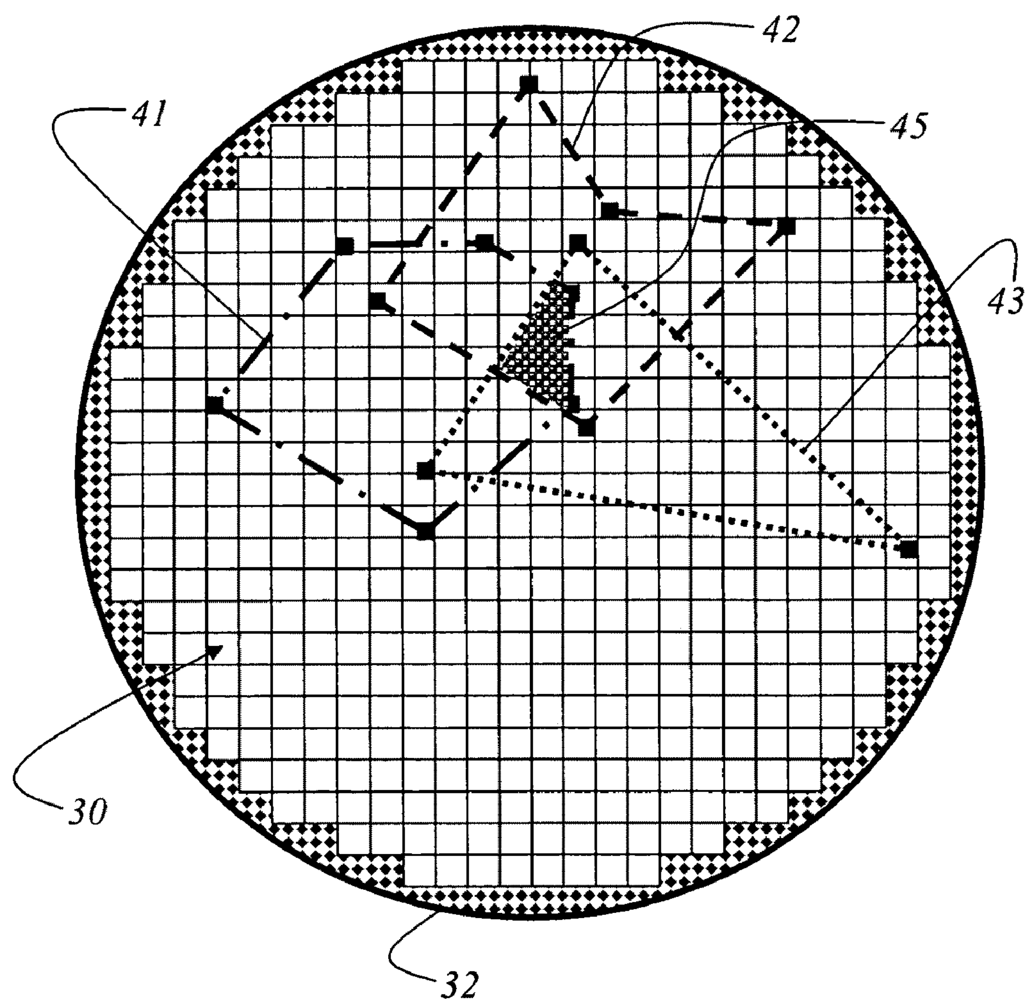
FIG. 4 shows an image of the front-side of a wafer having several overlapping regions defined thereon.

FIG. 4 shows a top view of the front-side 30 of a wafer 32 having several polygons 41, 42 and 43 defined on its surface. The polygons 41, 42 and 43 are positioned such that they have a common overlapping region 45. In the representation shown, the common overlapping region, also referred to as overlap region, is illustrated with a circular fill pattern. Different parameters may be set for each of the regions 41, 42, 43, which determine different detection sensitivities for detecting these regions. The detection sensitivity of each region differs from the rest of the wafer such that the detection sensitivity within the regions is less than for the rest of the wafer. It is to be noted with respect to the overlap region 45 that the detection sensitivity as specified for the region deposited on the top of the stack of the regions 41, 42 and 43 is used for this region. In the present case, the topmost region is the region identified by reference numeral 43. The order of the regions 41, 42 and 43 may be changed at any time by means of the input means.

Figure 5:
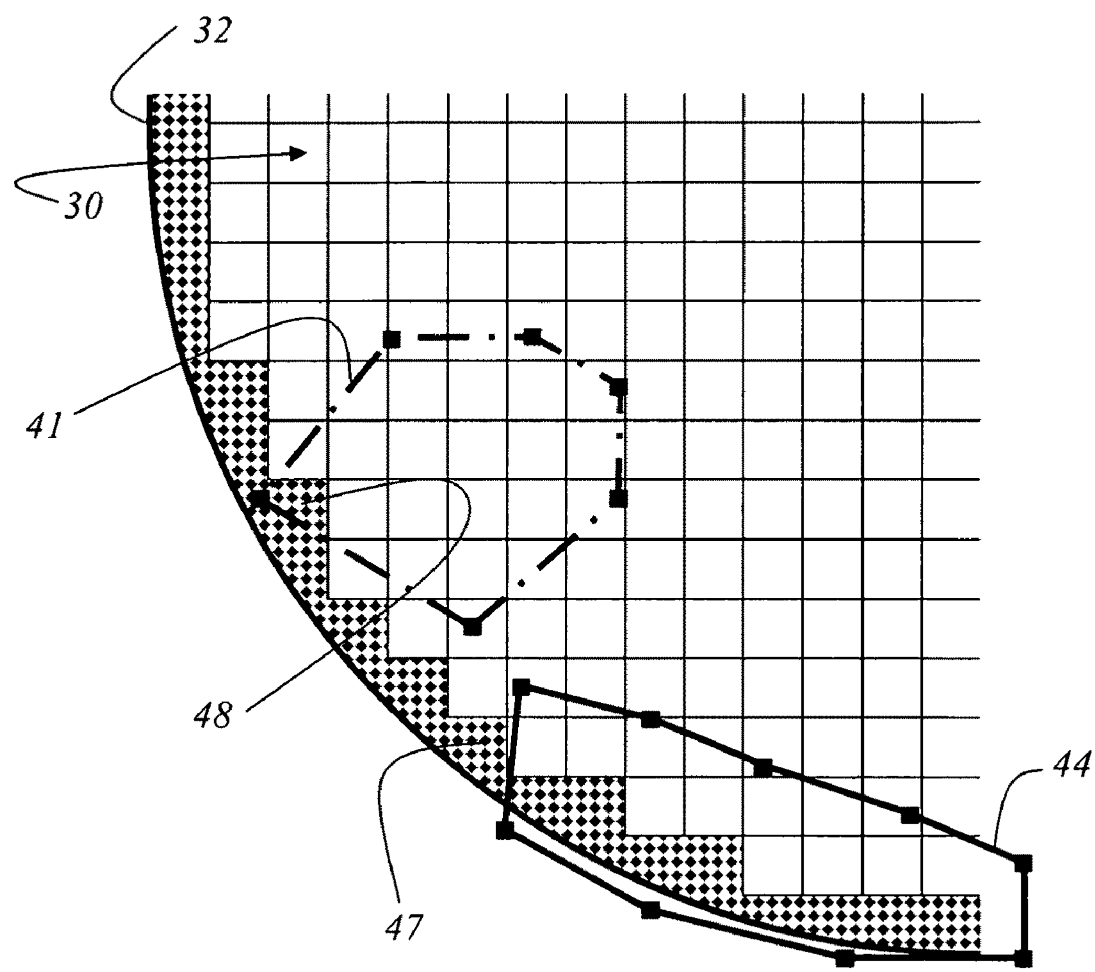
FIG. 5 shows a section of the image of the front-side of a wafer, wherein the region with a different detection sensitivity overlaps with the edge region of the wafer.

FIG. 5 shows a section of the edge region of a wafer 32. The region 41 to be inspected with a different detection sensitivity than the rest of the front-side 30 of the wafer 32 is located so close to the edge of the wafer that it overlaps with a region 47 where no structures are patterned. The polygon 41 thus overlaps with the edge region 47 of the wafer where no chip is patterned. This overlap 48 thus represents a region where no detection is performed. Another possibility is shown by region 44 in FIG. 5. The region 44 includes a large part of the edge region 47 of the wafer 32. The polygon 44 thus overlaps with the edge region 47 of the wafer where no chips are patterned. The detection in this region may be such that the detection is only performed in the region of the polygon not containing any chips. It is thus possible to obtain a more precise or adapted detection of the edge region 47 of the wafer.

Figure 6:
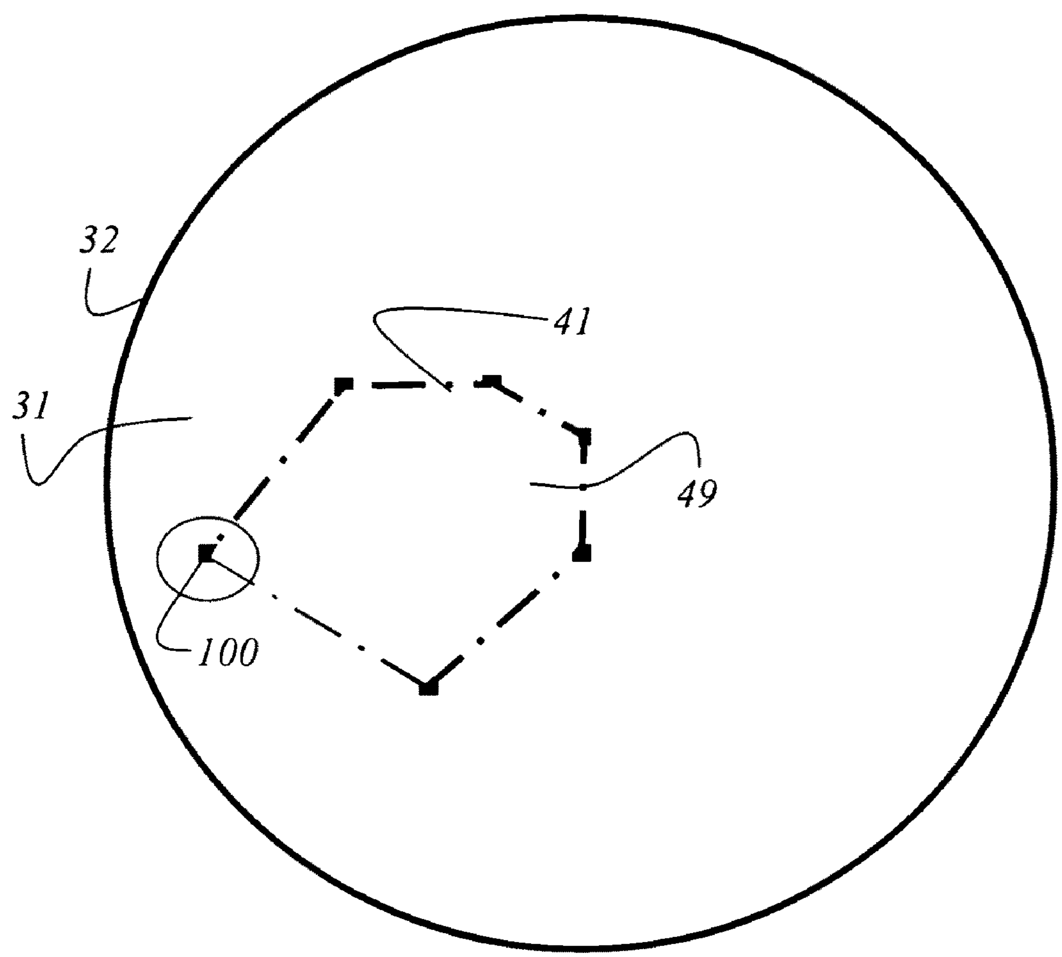
FIG. 6 schematically shows the image acquisition of the wafer on the backside of the wafer, wherein a region that is to be handled with a different detection sensitivity is defined on the backside of the wafer.

FIG. 6 shows the backside 31 of the wafer 32. A polygon 41 is also defined on the backside 31 of the wafer. The polygon 41 is characterized by a gray shading 49. There is thus performed a detection with other parameters in this region. It is also possible that the corner 100 marked by the circle may be shifted or deleted, or that another corner 100 may be added at this location. It is also possible that the whole polygon may be deleted with the marking of a corner 100 of the polygon.

The suggested method allows forming the regions where a detection with different sensitivity is performed in the shape of polygons or rectangles or any other shape. The regions may be formed on any surface of the wafer. It should further be possible to set the sensitivity for the detection between 0 and 100% for each polygon. This detection sensitivity should also be set for each type of detection.

Figure 7:
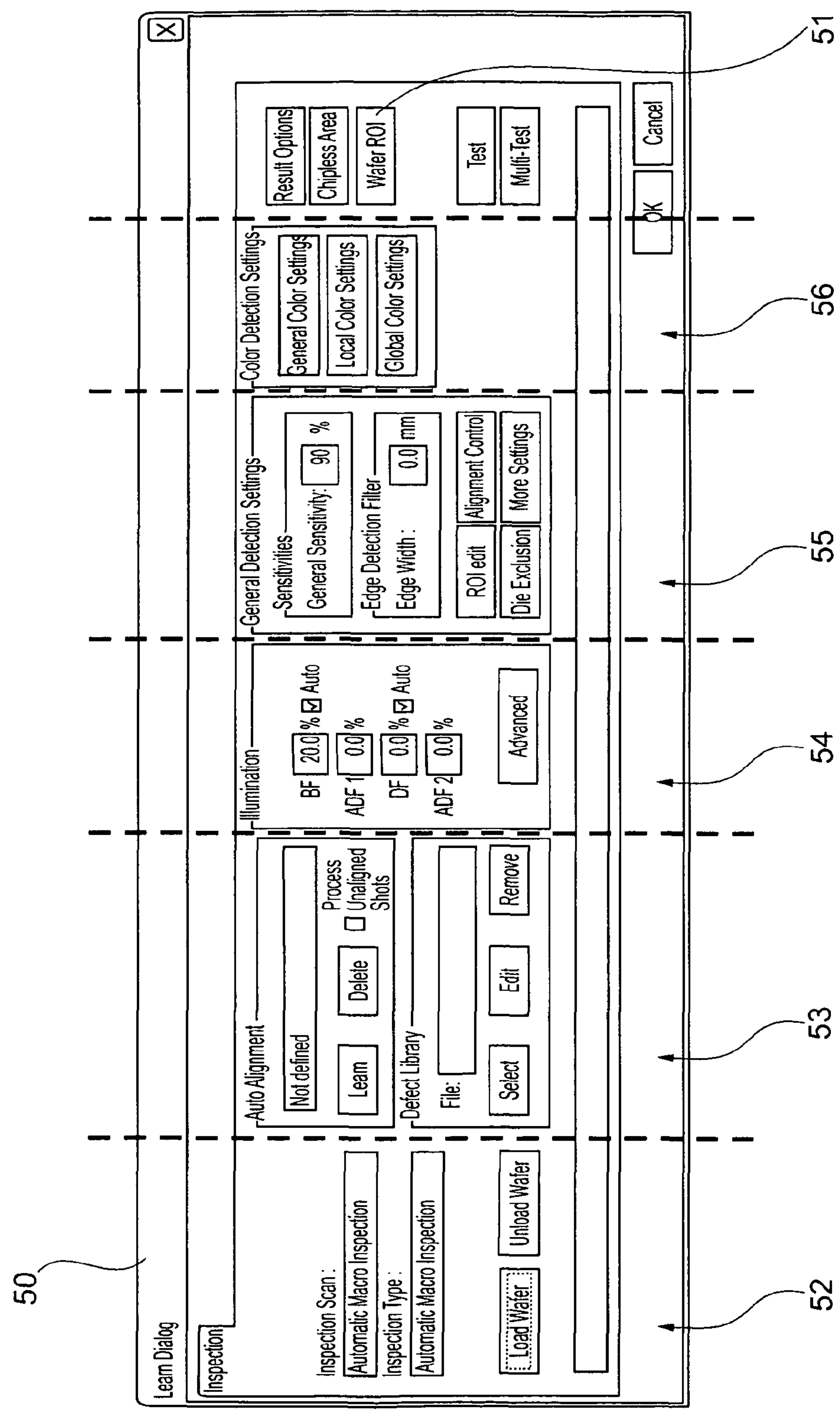
FIG. 7 shows a representation of a first window displayed to the user on the display of the device to allow input for the detection of the regions on the surface of a wafer with different detection sensitivity (in this window, the detection on the front-side of the wafer is described)

FIG. 7 shows a first window 50 that may be displayed to the user on the display 7. The functionality that, on the wafer, regions may be defined that are detected with different detection sensitivity may be created in the first window by means of a button 51. The button 51 is labeled "Wafer ROI". A further plurality of parameters and types of detection may be set in the first window 50. In a first section 52, the type of scanning for the surface of the wafer may be set and/or displayed. A second window 53 shows whether the wafer is aligned by an auto-alignment method. A third section 54 of the window 50 shows the setting for the illumination. A fourth section 55 of the window 50 shows general settings for the detection. A fifth section 56 of the window shows settings for the color detection.

Figure 8:
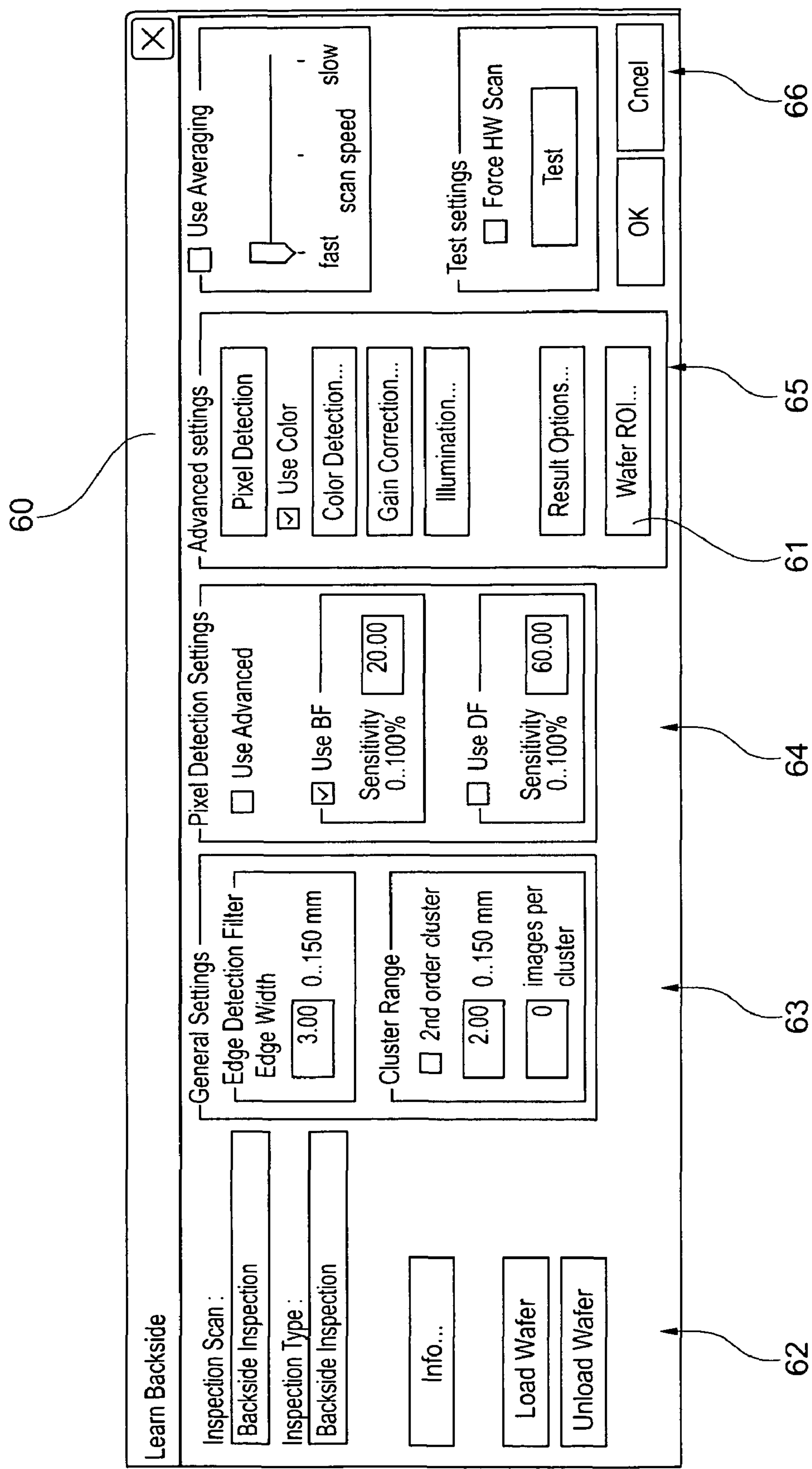
FIG. 8 shows a second window also displayed to the user on the display, via which the user may supply input regarding the detection sensitivity (in this window, the detection on the backside of the wafer is described)

FIG. 8 shows a second window 60 also displayed to the user on the display. This window serves for setting the detection on the backside of the wafer. The window 60 also comprises a button labeled "Wafer ROI". Furthermore, the window 60 is also divided into a first section 62, a second section 63, a third section 64, a fourth section 65 and a fifth section 66. The first section 62 of the window indicates what type of inspection is used. In the embodiment shown, backside inspection is used. The second section 63 of the window 60 displays general settings to the user. Settings for the pixel detection may be input in the third section 64 of the window 60. Further settings, such as color detection or gain correction, may be input in the fourth section 65 of the window 60. The fourth section 65 of the window 60 also contains the button labeled "Wafer ROI". In the fifth section 66 of the window 60, averaging may be performed.

Figure 9:
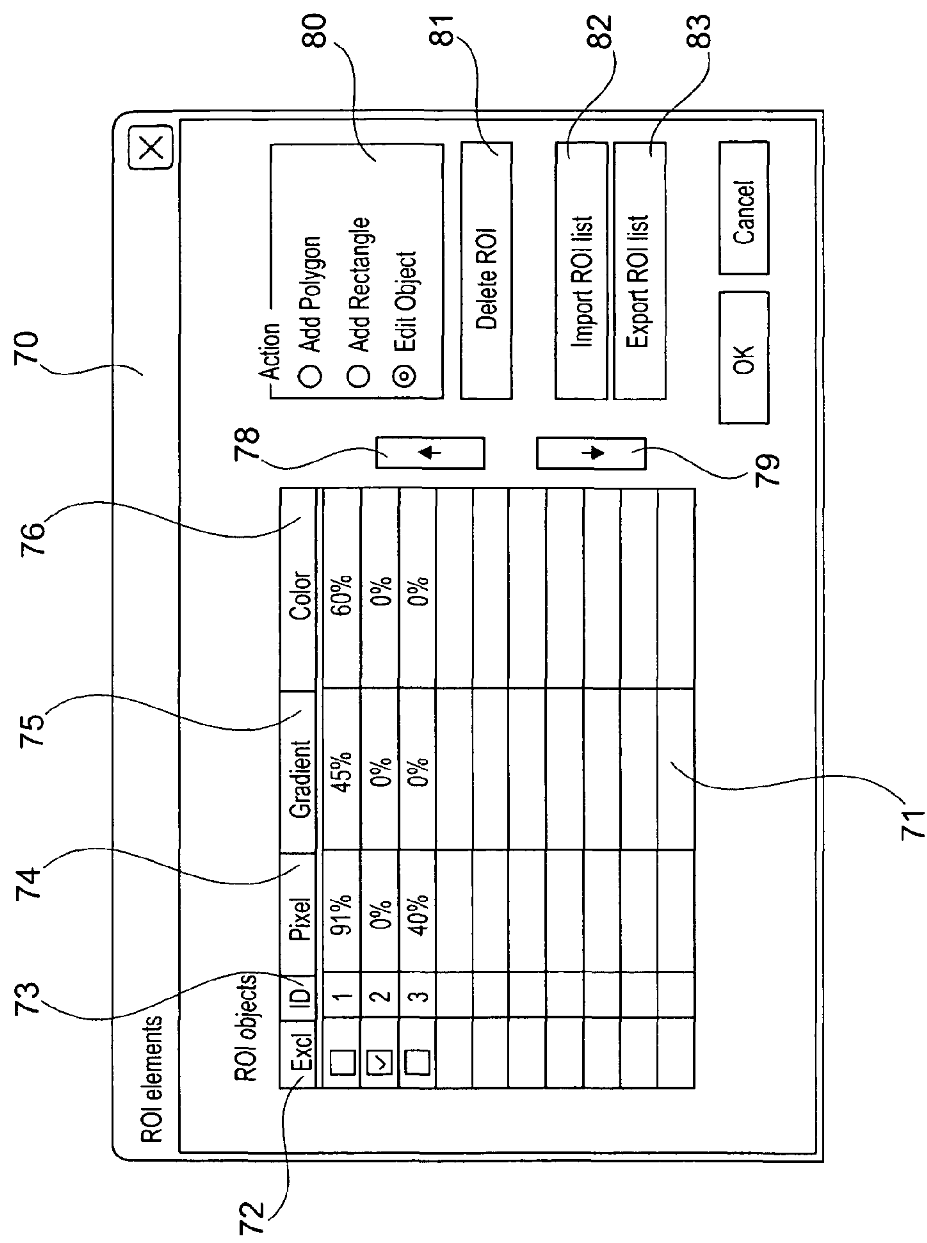
FIG. 9 shows a further window displayed to the user on the display, via which the user may select various regions with different detection sensitivities and may modify their parameters.

When the settings for the types of detection (front-side detection, backside detection or wafer edge detection) have been input, the user presses the button labeled "Wafer ROI", as mentioned above. When the button has been pressed, a third window 70 is displayed to the user on the display. This dialog window may be used to specify the definition of the polygons and the configuration of the parameters with which the detection may be performed within each polygon. In the third window 70, a list is displayed to the user, which includes the individual polygons defined on the surface of the wafer. In the first column 72 of the list 71, several check boxes are provided with the help of which a polygon may, for example, be excluded from detection. In the embodiment shown in FIG. 9, the polygon having the identification number 2 is, for example, excluded from detection. The exclusion is effected by putting a checkmark into the check box in front of the identification number 73 of the polygon. The sensitivity in the pixel detection may be set in the third column. The sensitivity for the gradient detection of the individual polygons may be set in the fourth column 75. The sensitivity of the polygons for the color detection may be set in the fifth column 76. Next to the list 71, an upward arrow 78 and a downward arrow 79 are illustrated. When, for example, the upward arrow 78 is actuated, the polygon marked in the list 71 is moved upward by one position. The same applies analogously to the actuation of the downward arrow 79. In the third window 70, there is further provided a subwindow 80 with which several actions may be selected. For example, the actions "Add Polygon" or "Add Rectangle" or "Edit Object" may be selected in the subwindow. If, for example, the button "Add Polygon" is selected, the surface or the region of the surface of the wafer is displayed to the user on the display, and the user may add a polygon in the way described above. When the user has confirmed the completion of the polygon with the right mouse button, this new polygon is added to the list 71 in the third window. The same happens when the user actuates the action "Add Rectangle". When the user actuates the menu item "Edit Object", all polygons in the list 71 may be modified or edited. With the help of the actuation button "Delete ROI", a region previously selected from the list may be deleted from the list and from the image representation of the surface of the wafer with the different regions (polygons or rectangles). The button "Import ROI list" 82 allows the user to import a previously stored list of regions (ROI) and to retrieve all previously set parameters. The imported polygons or regions and the associated parameters are added to the end of the list 71. Old values are not overwritten. The further actuation button 83 "Export ROI list" allows the user to store a created list of regions (polygons and/or rectangles) under a name chosen by the user.

The invention has been described with reference to particular embodiments. However, it is contemplated that modifications and changes may be made without departing from the scope of the following claims.

What is claimed is:

1. A method for inspecting a surface of a wafer with regions of different detection sensitivity, comprising the steps of:

acquiring an image of the surface of the wafer with the help of a detector;

displaying the image of the wafer on a display;

defining via the display using an input unit at least one region on the surface of the wafer that is subjected to a different detection sensitivity than the rest of the surface of the wafer, wherein the detection sensitivity specified for the regions on the surface is a percentage less than the detection sensitivity for the surface of the wafer without the regions with the different detection sensitivity; and specifying parameters or a way of acquiring the image of the surface of the wafer for the regions on the surface of the wafer to be handled with a different detection sensitivity, also by using the input unit;

wherein the at least one region of the surface of a wafer detected with a different detection sensitivity is defined by a polygon or a rectangle or an object which is edited by the user.

2. The method of claim 1 wherein the surface of the wafer is defined as a front-side of the wafer or as a backside of the wafer.

3. The method of claim 1 wherein a user interface is displayed on the display allowing a user to set the parameters necessary for a detection and provide settings for image acquisition and image evaluation.

4. The method of claim 3 wherein a first window is displayed on the user interface, via which input regarding a macro-detection of the wafer is supplied, and wherein a button is provided, via which the inspection of the surface of a wafer with regions of different detection sensitivity is initialized.

5. The method of claim 4 wherein a second window is displayed on the user interface, via which input regarding a macro-detection of a backside of the wafer is supplied, and wherein a button is provided, via which the inspection of the selected surface of the wafer with regions of different detection sensitivity is initialized.

6. The method of claim 1 wherein the regions defined on the surface of the wafer that are examined with a different detection sensitivity are modified or deleted by an input into the input unit.

7. The method of claim 1 wherein, in the case that the region on the surface of the wafer to be examined with a different detection sensitivity is a polygon, the polygon is created such that more than three corner points are created in the image of the surface of the wafer with the help of the input unit.

8. The method of claim 7 wherein, in the case of an overlap of the polygon with a region of the wafer not occupied by any chip, the detection is only performed in the region of the polygon containing the chips patterned on a front-side of the wafer.

9. The method of claim 8 wherein the region of the polygon not containing any chips on the surface of the wafer is displayed to the user in another color or with another pattern than the region of the polygon including the chips.

10. The method of claim 7 wherein, in the case of an overlap of the polygon with an edge region of the wafer not occupied by any chip, the detection is only performed in the region of the polygon not containing any chips patterned on a front-side of the wafer.

11. The method of claim 10 wherein the region of the polygon not containing any chips on the surface of the wafer is displayed to the user in another color or with another pattern than the region of the polygon including the chips.

12. The method of claim 1, wherein the detector is an area sensor.

13. The method of claim 1, wherein the detector is a line sensor.

14. A method for inspecting a surface of a wafer with regions of different detection sensitivity, comprising the steps of:

acquiring an image of the surface of the wafer with the help of a detector;

displaying the image of the wafer on a display;

defining via the display using an input unit at least one region on the surface of the wafer that is subjected to a different detection sensitivity than the rest of the surface of the wafer, wherein the detection sensitivity specified for the regions on the surface is a percentage less than the detection sensitivity for the surface of the wafer without the regions with the different detection sensitivity; and specifying parameters or a way of acquiring the image of the surface of the wafer for the regions on the surface of the wafer to be handled with a different detection sensitivity, also by using the input unit;

wherein a user interface is displayed on the display allowing a user to set the parameters necessary for a detection and provide settings for image acquisition and image evaluation;

wherein a first window is displayed on the user interface, via which input regarding a macro-detection of the wafer is supplied, and wherein a button is provided, via which the inspection of the surface of a wafer with regions of different detection sensitivity is initialized;

wherein a second window is displayed on the user interface, via which input regarding a macro-detection of a backside of the wafer is supplied, and wherein a button is provided, via which the inspection of the selected surface of the wafer with regions of different detection sensitivity is initialized;

wherein a third window is displayed on the user interface, via which the parameters regarding a shape of the at least one region inspected with a different detection sensitivity are set.

15. The method of claim 14 wherein several regions inspected with a different detection sensitivity are listed in the third window, wherein an identification number is assigned to each of the regions, that a percentage for a sensitivity of the pixel detection of the detector, a sensitivity of a gradient detection and a sensitivity for a local color detection is assigned to each of the regions for the inspection of a front-side of the wafer.

16. The method of claim 14 wherein several regions inspected with a different detection sensitivity are listed in the third window, wherein an identification number is assigned to each of the regions, that a percentage for a sensitivity of a pixel detection of the detector in the bright field, a sensitivity of a pixel detection in the dark field and a sensitivity for a color detection in the bright field is assigned to each of the regions for the inspection of the backside of the wafer.

17. The method of claim 14 wherein several regions, each of which is examined with a different detection sensitivity, are defined in the image of the surface of the wafer, wherein the shape of the regions and the detection parameters of the regions may be set as desired.

18. A method for inspecting a surface of a wafer with regions of different detection sensitivity, comprising the steps of:

acquiring an image of the surface of the wafer with the help of a detector;

displaying the image of the wafer on a display;

defining via the display using an input unit at least one region on the surface of the wafer that is subjected to a different detection sensitivity than the rest of the surface of the wafer, wherein the detection sensitivity specified for the regions on the surface is a percentage less than the detection sensitivity for the surface of the wafer without the regions with the different detection sensitivity; and specifying parameters or a way of acquiring the image of the surface of the wafer for the regions on the surface of the wafer to be handled with a different detection sensitivity, also by using the input unit;

wherein, if there are several overlapping regions each of which is to be examined with a different detection sensitivity and which differ with respect to the parameters for the detection sensitivity, the parameters corresponding to the region last input are valid for the region of overlap.

19. The method of claim 18 wherein the order of the overlapping regions may be changed by the input unit, wherein the parameters of a topmost region are then used for the detection in the overlap region.

* * * * *